(12) United States Patent
Cheng et al.

(10) Patent No.: US 10,137,163 B2
(45) Date of Patent: Nov. 27, 2018

(54) ***MELALEUCA QUINQUENERVIA* EXTRACTS AND USES OF THE SAME**

(71) Applicant: TAIWAN SUGAR CORPORATION, Tainan (TW)

(72) Inventors: Kun-Ching Cheng, Tainan (TW); Chun-Chin Chang, Tainan (TW); Jia-Jer Liou, Tainan (TW)

(73) Assignee: TAIWAN SUGAR CORPORATION, Tainan (TW)

( * ) Notice: Subject to any disclaimer, the term of this patent is extended or adjusted under 35 U.S.C. 154(b) by 282 days.

(21) Appl. No.: 14/992,332

(22) Filed: Jan. 11, 2016

(65) Prior Publication Data

US 2016/0120926 A1    May 5, 2016

Related U.S. Application Data

(62) Division of application No. 14/602,777, filed on Jan. 22, 2015, now abandoned.

(30) Foreign Application Priority Data

Jan. 27, 2014  (TW) .............................. 103102902 A

(51) Int. Cl.
*A61K 36/61*    (2006.01)

(52) U.S. Cl.
CPC .......... *A61K 36/61* (2013.01); *A61K 2236/00* (2013.01)

(58) Field of Classification Search
None
See application file for complete search history.

(56) References Cited

U.S. PATENT DOCUMENTS

2004/0151792 A1 *  8/2004  Tripp .................... A61K 31/12
                                                         424/745

OTHER PUBLICATIONS

El Manawaty (International Journal of Pharmacy and Pharmaceutical Sciences (2013), vol. 5, supp. 2, pp. 178-183).*
Tao Feng et al., "The Development of a Functional Assay System of Wnt/p—Catenin Signal Pathway," Journal of Chongqing Medical University; Apr. 2004 pp. 413-416, vol. 29, No. 4.
Hans Clevers et al., "Wnt/b-Catenin Signaling and Disease," Cell 149; Jun. 2012, pp. 1192-1205.
Hans Clevers, "Wnt/β-Catenin Signaling in Development and Disease," Cell 127; Nov. 2006, pp. 469-480.
Jeffrey R Miller et al., "Mechanism and Function of Signal Transduction by the Wnt/b-Catenin and Wnt/Ca2+ Pathways," Stockton Press ; 1999, pp. 7860-7872.
Jeonghee Surh et al., "Anti-oxident and Anti-inflammatory Activities of Butanol Extract of Melaleuca leucadendron", (Prev. Nutr. Food Sci. (2012), vol. 17, pp. 22-28).
Taiwanese Office Action corresponding to Application No. 103102902; dated Aug. 21, 2015.
Tzong-Huei Lee et al., "Inhibitory Effects of Glycosides from the Leaves of Melaleuca quinquenervia on Vascular Contraction of Rats" Planta Med 2002; 68(6):492-496.
United States Department of Agriculture [online][accessed Oct. 2015] http://plants.usda.gov/core/profile?symbol=mequm, Plants Profile for Melaleuca Quinquenervia (punktree).
United States Non Final Office Action corresponding to U.S. Appl. No. 14/602,777; dated Oct. 19, 2015.

* cited by examiner

*Primary Examiner* — Susan Hoffman
(74) *Attorney, Agent, or Firm* — Cantor Colburn LLP

(57) ABSTRACT

A *Melaleuca quinquenervia* extract and its uses are provided. The extract is extracted by a first polar solvent, wherein the first polar solvent is a C3-C6 ethanol. The extract is especially useful for inhibiting the Wnt/β-catenin signaling pathway.

16 Claims, No Drawings

MELALEUCA QUINQUENERVIA EXTRACTS AND USES OF THE SAME

CROSS-REFERENCE TO RELATED APPLICATIONS

The present application is a divisional application of U.S. patent application Ser. No. 14/602,777, filed on Jan. 22, 2015, now abandoned, the entire contents of which are incorporated herein by reference. The Ser. No. 14/602,777 application claimed the benefit of the date of the earlier filed Taiwanese Patent Application No. 103102902 filed on Jan. 27, 2014, priority to which is also claimed herein, and the contents of which are also incorporated by reference herein.

BACKGROUND OF THE INVENTION

Field of the Invention

The present invention relates to a *Melaleuca quinquenervia* extract and uses of the same. The extract is useful for inhibiting Wnt/β-catenin signal transduction pathway, and particularly useful for inhibiting the transcription activity of β-catenin and/or inhibiting the combination of β-catenin and T cell factor/lymphoid enhancer factor (TCF/LEF).

Description of the Related Art

A tumor is referred to as abnormal lesions of cells. Such lesions are caused by a variety of carcinogenic factors that affect the normal regulation of cells in a local tissue of human body at the gene level and result in abnormal proliferation and lumping of cells, called a "tumor." A "cancer" is the most common tumor type in which the abnormal proliferating cancer cells will not only assemble to become lumps, but also spread and metastasize to other tissues or organs in the body. The proliferation and metastasis of cancer cells may lead to severe abnormal physiological functions that are difficult to be cured. Therefore, cancer has been one of the top causes of human death over recent years.

Traditional treatments for tumors include surgical treatment, chemical treatment, radiation treatment, etc. However, surgical excision of tumors cannot effectively cure tumors, because incompletely excised tumor cells may continue growing and make the condition of the patient worse. Therefore, in addition to surgical excision, tumors must be treated concurrently with other treatment(s), such as chemical or radiation treatment. Chemical treatment is conducted by exposing tumor cells that are growing rapidly to chemicals with cytotoxic effects. However, most medicaments used in chemical treatment also have harmful effects on normal cells. For example, chemical treatment usually induces severe side-effects in cancer patients, which include emesis, baldness, fatigue, hemorrhage, anemia, etc. Radiation treatment can kill tumor cells by breaking the DNA sequence of cancer cells that divide more rapidly and are more sensitive to radiation than normal cells. However, high energy radiation will simultaneously irradiate normal cells when being used to destroy tumor cells, and such irradiation will result in side-effects, such as leukopenia, fatigue, insomnia, pain, inappetence, etc. In addition, the therapeutical effect of radiation treatment is poor for some patients in the late stage of the disease. Therefore, there is still a need in clinic for a method or medicament which can effectively treat tumors and increase the cure rate and/or reduce side-effects.

The present invention is a study for the above needs. The inventors of the present invention found that a *Melaleuca quinquenervia* extract is useful in inhibiting Wnt/β-catenin signal transduction pathway, and therefore can be used for providing a medicament for blocking the development of tumors.

SUMMARY OF THE INVENTION

An objective of the present invention is to provide a *Melaleuca quinquenervia* extract, which is prepared by extracting *Melaleuca quinquenervia* with a first polar solvent, wherein the first polar solvent is a C3-C6 alcohol.

Another objective of the present invention is to provide a pharmaceutical composition for inhibiting Wnt/β-catenin signal transduction pathway, wherein the pharmaceutical composition comprises a *Melaleuca quinquenervia* extract as described above.

A further objective of the present invention is to provide a method for inhibiting Wnt/β-catenin signal transduction pathway in a subject, comprising administering to the subject in need an effective amount of the above *Melaleuca quinquenervia* extract.

A yet objective of the present invention is to provide a method for inhibiting Wnt/β-catenin signal transduction pathway in a subject, comprising administering to the subject in need an effective amount of the above pharmaceutical composition.

The detailed technology and some preferred embodiments implemented for the subject invention are described in the following paragraphs for people skilled in this field to well appreciate the features of the claimed invention.

BRIEF DESCRIPTION OF THE DRAWINGS

None.

DETAILED DESCRIPTION OF THE INVENTION

The following will describe some embodiments of the present invention in detail. However, without departing from the spirit of the present invention, the present invention may be embodied in various embodiments and should not be limited to the embodiments described in the specification. In addition, unless otherwise state herein, the expressions "a", "the", or the like that are recited in the specification of the present invention (especially in the claims) should include both the singular and plural forms.

Wnt signal protein is a secretory glycoprotein involved in Wnt signal transduction pathway, wherein the receptor of Wnt signal protein is Frizzled (Frz). In the development of a subject, Wnt signal transduction pathway is closely related to the mechanisms of cell proliferation, differentiation, migration, polarization, apoptosis, etc. During the activation of Wnt signal transduction pathway, Wnt protein will combine with Frz to stabilize β-catenin in the cytoplasm. The combined Wnt protein and Frz will render β-catenin to accumulate largely in cytoplasm and to migrate to the nucleus and then combine with transcription factors, i.e., T cell factor/lymphoid enhancer factor (TCF/LEF), so as to regulate the transcription of downstream genes, such as the transcription of a variety of downstream genes related to the differentiation and proliferation of stem cells. Therefore, β-catenin plays a critical role in Wnt signal transduction pathway. The transcription activity of β-catenin is closely related to cell differentiation and proliferation (see Wnt/β-catenin signaling in development and disease. *Cell.* 2006 Nov. 3; 127(3):469-80; Wnt/β-catenin signaling and disease. *Cell.* 2012 Jun. 8; 149(6):1192-205; and Mechanism and function of signal transduction by the Wnt/β-catenin and Wnt/Ca$^{2+}$ pathways. *Oncogene.* 1999 Dec. 20; 18(55):7860-72, which are entirely incorporated hereinto by reference).

It is known that the abnormal transcription activity of β-catenin may lead to abnormal activation of Wnt transduction pathway, which causes the generation and development of a variety of tumors. For example, studies have found that the activity of Wnt signal transduction pathway is enhanced in over 90% rectal cancer patients, indicating that Wnt signal transduction pathway is closely related to the development of rectal cancer. In addition, the mutation and overexpression of β-catenin in cells can also be observed in a variety of other human tumors. Studies also showed that the carcinogenic mutations of β-catenin may induce the formation of tumors in transgenic animals, and β-catenin mutation can also be detected in tumors induced by carcinogenic factors and carcinogenic genes activation.

Accordingly, it is understood that the over activation of β-catenin is closely related to the development of tumors in the living body. If the activation of β-catenin can be inhibited, the development of tumors can be blocked. Therefore, if a component is effective in inhibiting the transcription activity of β-catenin, it can be used as a target medicine for anti-tumor.

The inventors of the present invention found that a *Melaleuca quinquenervia* extract can block Wnt/β-catenin signal transduction pathway by inhibiting the transcription activity of β-catenin and/or the combination of β-catenin and TCF/LEF, and thus, is useful for blocking the development of a tumor.

Accordingly, the present invention provides a *Melaleuca quinquenervia* extract, which is preferably prepared by extracting *Melaleuca quinquenervia* with a first polar solvent. The first polar solvent is preferably a C3-C6 alcohol, such as propanol, isopropanol, propanediol, n-butanol, isobutanol, tert-butanol, butanediol, n-pentanol, isopentanol, tert-pentanol, pentanediol, n-hexanol, cyclohexanol, hexanediol, and combinations thereof. In some embodiments of the present invention, n-butanol is used as the first polar solvent.

The *Melaleuca quinquenervia* extract of the present invention can be prepared by any suitable preparation methods. For example, before or after conducting the first polar solvent extracting step, one or more extracting steps with other suitable solvent(s) could be conducted. A concentration step can optionally be conducted to increase the yield of the extract.

According to some embodiments of the present invention, the *Melaleuca quinquenervia* extract of the present invention is prepared by a method comprising the following steps:
(a) extracting *Melaleuca quinquenervia* with a second polar solvent to provide a first extraction fluid;
(b) partitioning the first extraction fluid with a first polar solvent and collecting the first polar solvent phase; and
(c) optionally removing the first polar solvent from the first polar solvent phase,
wherein the second polar solvent is preferably water and/or a C1-C4 alcohol, such as methanol, ethanol, ethanediol, propanol, isopropanol, propanediol, n-butanol, isobutanol, tert-butanol, butanediol and combinations thereof; and is more preferably methanol, water or a mixture thereof.

In some embodiments of the present invention, the step (a) that extracts *Melaleuca quinquenervia* with the second polar solvent comprises:
(a1) extracting the *Melaleuca quinquenervia* with methanol to provide a methanol extraction fluid;
(a2) optionally concentrating the methanol extraction fluid to provide a concentrated solution; and
(a3) adding water into the concentrated solution to provide the first extraction fluid.

In the above described method for preparing the *Melaleuca quinquenervia* extract of the present invention, at least one of the following steps can optionally be conducted prior to the partitioning step (b):
(b1') partitioning the first extraction fluid with a C5-C8 alkane and removing the alkane phase; and
(b2') partitioning the first extraction fluid with ethyl acetate and removing the ethyl acetate phase,
wherein examples of C5-C8 alkane include, but are not limited to, n-pentane, isopentane, n-hexane, 2-methylpentane, 3-methylpentane, 2,2-dimethylbutane, 2,3-dimethylbutane, cyclohexane, petroleum ether, n-heptane, 2-methylhexane, 3-methylhexane, 2,2-dimethylpentane, 2,3-dimethylpentane, 2,4-dimethylpentane, 3,3-dimethylpentane, 3-ethylpentane, 2,2,3-trimethyl butane, n-octane, isooctane, and combinations thereof. Preferably, the C5-C8 alkane solvent is n-hexane.

The extract of the present invention can be provided from any part of *Melaleuca quinquenervia*, such as the roots, stems, leaves of *Melaleuca quinquenervia*, or combinations thereof. Preferably, the extract of the present invention is provided by extracting a leaf and/or a branch with leaves of *Melaleuca quinquenervia*.

As described above, the extract of the present invention is effective in inhibiting Wnt/β-catenin signal transduction pathway. Therefore, the present invention also provides a pharmaceutical composition for inhibiting Wnt/β-catenin signal transduction pathway, which comprises a *Melaleuca quinquenervia* extract. The characters and preparation of the *Melaleuca quinquenervia* extract are as described above.

The pharmaceutical composition of the present invention is useful for inhibiting Wnt/β-catenin signal transduction pathway, especially for inhibiting the transcription activity of β-catenin and/or the combination of β-catenin and TCF/LEF, and thus, can be used for blocking the development of any tumors related to Wnt/β-catenin signal transduction pathway, especially for inhibiting at least one tumor selected from the group consisting of rectal cancer, breast cancer, brain cancer, esophageal cancer and liver cancer.

The pharmaceutical composition of the present invention can be prepared in any suitable form and be administered by any suitable route. For example, the composition can be administrated to a subject by oral administration, subcutaneous injection, intravenous injection, etc., but is not limited thereby. Depending on the form and application, the pharmaceutical composition may further comprise a pharmaceutically acceptable carrier.

Taking the manufacture of a formulation suitable for oral administration as an example, the pharmaceutical composition may comprise a pharmaceutically acceptable carrier which has no adverse influence on the benefit of the *Melaleuca quinquenervia* extract, such as a solvent, an oily solvent, a diluent, a stabilizer, an absorption delaying agent, a disintegrant, an emulsifier, an antioxidant, a binder, a lubricant, and a moisture absorbent. The pharmaceutical composition can be provided as a formulation for the oral administration by any suitable methods, such as the formulation of a tablet, a capsule, a granule, powder, a fluid extract, a solution, a syrup, a suspension, an emulsion, a tincture, etc.

As for a formulation suitable for subcutaneous injection or intravenous injection, the pharmaceutical composition of the present invention may comprise one or more components such as an isotonic solution, a saline buffer solution (e.g. a phosphate buffer solution or a citrate buffer solution), a solubilizer, an emulsifier, other carriers, etc., to provide the pharmaceutical composition as an intravenous injection, an emulsion intravenous injection, a powder injection, a suspension injection, a powder-suspension injection, etc.

Optionally, the pharmaceutical composition of the present invention may further comprise additives such as a flavoring agent, a toner, a coloring agent, etc. to enhance the taste and visual appeal of the pharmaceutical composition. To improve the storability of the pharmaceutical composition, a suitable amount of a preservative, a conservative, an antiseptic, an anti-fungus reagent, etc. may also be added. Furthermore, the pharmaceutical composition may optionally comprise one or more other active components or be used in combination with a medicament comprising the one or more active components to further enhance the efficacy of the pharmaceutical composition or to increase the application flexibility and adaptability of the formulation of the pharmaceutical composition, as long as the other active components have no adverse effect on the desired effect of the *Melaleuca quinquenervia* extract. The active component can be an antioxidant (e.g. vitamin E), an immune modulator, etc.

Depending on the requirements of the subject, the pharmaceutical composition of the present invention can be applied with various administration frequencies, such as once a day, several times a day or once for days, etc.

The present invention will be further illustrated in detail with specific examples as follows. However, the following examples are provided only for illustrating the present invention, and the scope of the present invention is not limited thereby. The scope of the present invention is as set forth in the appended claims.

EXAMPLES

Example 1

Preparation of *Melaleuca quinquenervia* Extract

Leaves and branches with leaves of *Melaleuca quinquenervia* were air dried and smashed by a comminutor, and then processed by the following steps:
i). soaking and extracting 2250 g of smashed *Melaleuca quinquenervia* with methanol (100%) at room temperature for 2 days, and repeated 3 times to obtain a methanol extract;
ii). filtrating the methanol extract from step i) and concentrating under a vacuum to obtain a crude extract;
iii). adding 1500 ml of pure water to the crude extract of step ii) and mixing the mixture uniformly by ultrasonic oscillation to obtain a methanol extraction fluid;
iv). partitioning the methanol extraction fluid of step iii) by adding 2000 ml of n-hexane thereinto, and then removing the n-hexane phase;
v). partitioning the extraction fluid of step iv) by adding 1800 ml of ethyl acetate thereinto, and then removing the ethyl acetate phase;
vi). partitioning the extraction fluid of step v) by adding 1800 ml of n-butanol thereinto, and then collecting the n-butanol phase; and
vii). concentrating the n-butanol phase collected in step vi) under vacuum to remove the residual solvent and obtain a *Melaleuca quinquenervia* extract.

Example 2

Analysis of the Activity of *Melaleuca quinquenervia* Extract on Inhibiting Wnt/β-catenin Signal Transduction Pathway An analysis system for analyzing the activity of Wnt/β-catenin signal transduction pathway was used in this example as a screening platform (provided from Food Industry Research and Development Institute, Taiwan) for components with anti-tumor activity. The screening platform comprises a human cell line (referred to as "293-bc-GFP cell line") which can express a fusion protein of β-catenin and green fluorescent protein (GFP) as a reporter gene (referred to as "β-catenin-GFP-fusion protein"). The preparation method of the human cell line for expressing β-catenin-GFP-fusion protein has been described in detail by references (see The development of a functional assay system of Wnt/β-catenin signal pathway, *Journal of Chongqing Medical University.* 29: 413-416; 2004, which is entirely incorporated hereinto by reference). In addition, a luciferase (Luc) could be used as a reporter gene to replace the above GFP to provide a human cell line (referred to as "293-bc-Luc cell line") which can express a fusion protein of β-catenin and Luc (referred to as "β-catenin-Luc-fusion protein").

The principle of the screening platform for components with anti-tumor activity is summarized as follows. Generally, β-catenin in a cell is very unstable and can be degraded by protein degradation system easily, and thus, the expression level of free β-catenin in a cell is very low. Therefore, the β-catenin-GFP-fusion protein or the β-catenin-Luc-fusion protein in the screening platform described above would degrade rapidly after expression, and thus, almost no or only weak green fluorescence or luminescence can be observed by a fluorescent microscope. Accordingly, before using the above screening platform to screen medicaments for inhibiting β-catenin expression, a factor for stabilizing the β-catenin-GFP-fusion (such as lithium) can be added to the screening platform to increase the expression of the fusion protein to a detectable level (i.e. green fluorescence or luminescence was visible by a fluorescent microscope), and then to screen active components with anti-tumor activity. When screening active components with anti-tumor activity, a medicament to be tested is added into the screening platform. If the green fluorescence or luminescence is decreased or disappeared, this indicates that the tested medicament can inhibit β-catenin transcription activity or the combination of β-catenin and TCF/LEF, and thus, is useful for inhibiting Wnt/β-catenin signal transduction pathway. In addition, the medicament can be used as an upstream regulatory factor of the gene expression of β-catenin in a human tumor and can be used as medicament that inhibits the development of a tumor.

In this example, the above described screening platform for an anti-tumor gene was used to analyze the activity of the *Melaleuca quinquenervia* extract prepared in Example 1 on inhibiting Wnt/β-catenin signal transduction pathway. The results are showed in Table 1.

TABLE 1

| | Luminescence (Luc) (as compared to the control group) | |
|---|---|---|
| | Average (%) | Standard deviation (%) |
| *Melaleuca quinquenervia* extract (25 µg/ml) | 60% | 2% |

As shown in Table 1, as compared to the control group (i.e. the group that was not treated with *Melaleuca quinquenervia* extract; the average luminescence intensity of the control group in the screening platform for anti-tumor gene was set at 100%), the average luminescence intensity of the experiment group treated with 25 μg/ml *Melaleuca quinquenervia* extract was reduced to 60%. The result indicated that the inhibition rate of the *Melaleuca quinquenervia* extract of the present invention on Wnt/β-catenin signal transduction pathway was about 40%.

Example 3

Cytotoxicity Test of *Melaleuca quinquenervia* Extract 3-(4,5-dimethylthiazol-2-yl)-2,5-diphenyl tetrazolium bromide (referred to as "MTT") was used to test the survival rate of the 293-bc-Luc cell line treated with the *Melaleuca quinquenervia* extract prepared from Example 1. First, 293-bc-Luc cell line was cultured with 0.1 ml DMEM culture medium (containing 10% fetal bovine serum, 100 unit/ml penicillin and 100 μg/ml streptomycin) at an initial cell number of $5 \times 10^4$ cells per well in 96-well culture plate in an incubator with 37° C., 5% $CO_2$ overnight. After the cells attached to the culture plate, the original culture medium was removed and fresh 0.1 ml of DMEM medium and 25 μg/ml *Melaleuca quinquenervia* extract prepared from Example 1 were added to each well of the culture plate and cultured in an incubator with 37° C., 5% $CO_2$ for 24 hours. Thereafter, the culture medium was removed. 20 ml of MTT solution (5 mg/ml) was added to each well of the culture plate and placed in an incubator at 37° C., 5% $CO_2$ for 2.5 hours for reaction. Then, all of the culture medium was removed. 150 μl of DMSO was added to each well of the plate to react at 37° C. for 10 minutes. The absorbance at 490 nm wavelength of the sample was measured, and the survival rate of the cells treated with the *Melaleuca quinquenervia* extract was calculated. The results are shown in Table 2.

TABLE 2

| | Cells survival rate (MTT, $OD_{490}$) (as compared to the control group) | | Luminescence (as shown in Table 1)/cell survival rate |
|---|---|---|---|
| | Average % | Standard error % | % |
| *Melaleuca quinquenervia* extract (25 μg/ml) | 91% | 8% | 65% |

As shown in Table 2, as compared to the control group (without *Melaleuca quinquenervia* extract treatment), the survival rate of the 293-bc-Luc cells treated with 25 μg/ml *Melaleuca quinquenervia* extract was 90%. The result indicated that the *Melaleuca quinquenervia* extract had almost no cytotoxicity to the 293-bc-Luc cells. In addition, the luminescence ratio (60%) of the experiment group measured in Example 2 was divided by the cells' survival rate of the present example. The calculated ratio of the luminescence (%)/the cells survival rate (%) was about 65% (i.e., 60/91× 100%=65%). The ratio of the luminescence (%)/the cells survival rate (%) ranged from 25% to 75%. The cells' survival rate was higher than 80%. The results indicated that the *Melaleuca quinquenervia* extract had an anti-tumor activity.

Based on the above results and explanation, the *Melaleuca quinquenervia* extract of the present invention can be used for inhibiting the activation of Wnt/β-catenin signal transduction pathway and thus, can be used for providing a medicament for blocking the development of tumors.

What is claimed is:

1. A method for inhibiting Wnt/β-catenin signal transduction pathway in a subject comprising administering to the subject in need an effective amount of a *Melaleuca quinquenervia* extract, wherein the extract is prepared by a method comprising the following steps:
    (a) extracting *Melaleuca quinquenervia* with a second polar solvent to provide a first extraction fluid, wherein the second polar solvent is methanol, water, or a combination thereof;
    (b1') partitioning the first extraction fluid with a C5-C8 alkane and removing the alkane phase;
    (b2') partitioning the product of step (b1') with ethyl acetate and removing the ethyl acetate phase;
    (b) partitioning the product of step (b2') with a first polar solvent and collecting the first polar solvent phase, wherein the first polar solvent is a C3-C6 alcohol; and
    (c) optionally removing the first polar solvent from the first polar solvent phase.

2. The method as claimed in claim 1, wherein the first polar solvent comprises butanol.

3. The method as claimed in claim 1, wherein the first polar solvent is n-butanol.

4. The method as claimed in claim 1, wherein the step (a) includes:
    (a1) extracting the *Melaleuca quinquenervia* with methanol to provide a methanol extraction fluid;
    (a2) optionally concentrating the methanol extraction fluid to obtain a concentrated solution; and
    (a3) adding water into the concentrated solution to obtain the first extraction fluid.

5. The method as claimed in claim 1, wherein the extract is prepared by extracting a leaf and/or a branch with leaves of *Melaleuca quinquenervia*.

6. The method as claimed in claim 1, which is for inhibiting the transcription activity of β-catenin and/or inhibiting the combination of β-catenin and T cell factor/lymphoid enhancer factor (TCF/LEF).

7. The method as claimed in claim 6, which is for blocking the development of a tumor.

8. The method as claimed in claim 7, wherein the tumor is at least one of rectal cancer, breast cancer, brain cancer, esophageal cancer and liver cancer.

9. A method for inhibiting Wnt/β-catenin signal transduction pathway in a subject comprising administering to the subject in need an effective amount of a pharmaceutical composition, wherein the pharmaceutical composition comprises a *Melaleuca quinquenervia* extract and the extract is prepared by a method comprising the following steps:
    (a) extracting *Melaleuca quinquenervia* with a second polar solvent to provide a first extraction fluid, wherein the second polar solvent is methanol, water, or a combination thereof;
    (b1') partitioning the first extraction fluid with a C5-C8 alkane and removing the alkane phase;
    (b2') partitioning the product of step (b1') with ethyl acetate and removing the ethyl acetate phase;
    (b) partitioning the product of step (b2') with a first polar solvent and collecting the first polar solvent phase, wherein the first polar solvent is a C3-C6 alcohol; and
    (c) optionally removing the first polar solvent from the first polar solvent phase.

10. The method as claimed in claim 9, wherein the first polar solvent comprises butanol.

11. The method as claimed in claim 9, wherein the first polar solvent is n-butanol.

12. The method as claimed in claim 9, wherein the step (a) includes:
   (a1) extracting the *Melaleuca quinquenervia* with methanol to provide a methanol extraction fluid;
   (a2) optionally concentrating the methanol extraction fluid to obtain a concentrated solution; and
   (a3) adding water into the concentrated solution to obtain the first extraction fluid.

13. The method as claimed in claim 9, wherein the extract is prepared by extracting a leaf and/or a branch with leaves of *Melaleuca quinquenervia*.

14. The method as claimed in claim 9, which is for inhibiting the transcription activity of β-catenin and/or inhibiting the combination of β-catenin and T cell factor/lymphoid enhancer factor (TCF/LEF).

15. The method as claimed in claim 14, which is for blocking the development of a tumor.

16. The method as claimed in claim 15, wherein the tumor is at least one of rectal cancer, breast cancer, brain cancer, esophageal cancer and liver cancer.

* * * * *